(12) United States Patent
Walter-Engelsma

(10) Patent No.: US 11,904,112 B2
(45) Date of Patent: Feb. 20, 2024

(54) CATHETER MOUNTING ARRANGEMENT FOR SECURING A CATHETER TO A PATIENT AND A METHOD OF MAINTAINING THE SECURING AND INTEGRITY IN FLUID FLOW WITHIN THE CATHETER WHILE MOUNTED TO THE PATIENT

(71) Applicant: GET IP PTY LTD, Goodwood (AU)

(72) Inventor: Shannon Merryl Jane Walter-Engelsma, Adelaide (AU)

(73) Assignee: P6 Medical Pty Ltd, Goodwood (AU)

( * ) Notice: Subject to any disclaimer, the term of this patent is extended or adjusted under 35 U.S.C. 154(b) by 979 days.

(21) Appl. No.: 17/052,532

(22) PCT Filed: Sep. 27, 2018

(86) PCT No.: PCT/AU2018/051061
§ 371 (c)(1),
(2) Date: Nov. 3, 2020

(87) PCT Pub. No.: WO2019/075509
PCT Pub. Date: Apr. 25, 2019

(65) Prior Publication Data
US 2023/0218864 A1    Jul. 13, 2023

(30) Foreign Application Priority Data
Oct. 17, 2017   (AU) .................. 2017904190

(51) Int. Cl.
*A61M 25/02*       (2006.01)

(52) U.S. Cl.
CPC ....... *A61M 25/02* (2013.01); *A61M 2025/024* (2013.01); *A61M 2025/028* (2013.01); *A61M 2025/0273* (2013.01)

(58) Field of Classification Search
CPC ............ A61M 25/02; A61M 2025/024; A61M 2025/0273; A61M 2025/028;
(Continued)

(56) References Cited

U.S. PATENT DOCUMENTS 4,669,463  A  *  6/1987  McConnell  .......  A61M 16/0463
                                                128/207.14
6,206,885  B1 *  3/2001  Ghahremani  ......  A61B 17/1695
                                                128/DIG. 26
(Continued)

*Primary Examiner* — Brandy S Lee
*Assistant Examiner* — Phoebe Anne Staton
(74) *Attorney, Agent, or Firm* — Todd Martin

(57) ABSTRACT

A catheter mounting arrangement including a main housing unit configurable to be fastenable around a catheter that has been inserted into a fluid cavity within a patient. The main housing unit includes a slot that defines a longitudinal opening through which an uninserted section of tubing of the inserted catheter is passable there through. The main housing unit and inserted catheter includes an engagement arrangement so that once the uninserted section of the tubing of the inserted catheter has passed through the slot there is a fixed vertical support of the catheter within the main housing unit so that the uninserted section of tubing of the inserted catheter remains substantially upright and/or substantially free of kinks or bends.

13 Claims, 7 Drawing Sheets

(58) Field of Classification Search
CPC .......... A61M 16/0497; A61M 39/0247; A61M 25/0105; A61M 2039/1033; A61M 2039/1038; A61M 5/1418; A61M 5/1415; A61M 25/0113; A61J 15/0053
See application file for complete search history.

(56) References Cited

U.S. PATENT DOCUMENTS

| | | | |
|---|---|---|---|
| 2003/0028199 A1* | 2/2003 | Ghahremani | A61B 17/1695 |
| | | | 606/108 |
| 2016/0279367 A1* | 9/2016 | Kanowitz | A61M 16/0497 |
| 2017/0143937 A1* | 5/2017 | Griffin | A61B 17/3439 |

* cited by examiner

CATHETER MOUNTING ARRANGEMENT FOR SECURING A CATHETER TO A PATIENT AND A METHOD OF MAINTAINING THE SECURING AND INTEGRITY IN FLUID FLOW WITHIN THE CATHETER WHILE MOUNTED TO THE PATIENT

TECHNOLOGICAL FIELD

This invention relates to an arrangement and method for mounting a catheter to a patient and in particular to an arrangement that will allow a fastening of the catheter once the catheter is inserted into the patient by way of an inherent design that will prevent the mounted catheter from becoming easily dislodged or withdrawn from the insertion location of the catheter in the patient and to provide such a mounting arrangement that will also maintain integrity of fluid flow within the tubing of the catheter while the catheter remains inserted into the patient.

BACKGROUND ART DISCUSSION

While from here on after, this invention is placed in the context of paracentesis procedures, the scope of this invention should not be interpreted so restrictively.

The catheter mounting arrangement of this invention, which will provide for a fixed mounting or positioning of the catheter with the body cavity within the patient from which it extends, can also be utilised in other applications where a catheter is required to drain or provide fluid to and from a living human or animal.

For the most part a paracentesis procedure requires a patient to be prepped and thereafter a needle incorporated within the catheter is then inserted into the abdominal cavity.

Problems arise however when the needle is required to be removed, leaving behind a section of the catheter within the body and an external section of the catheter which the fluid is required to pass there through to drain the fluid from the patient accordingly.

The procedure of removal of the needle can be painful and if performed improperly it could inadvertently incorrectly reposition the catheter with respect to the abdominal cavity from which fluid is required to be drained.

Still even further, poor removal of the needle from the inserted catheter could unintentionally puncture adjacent organs.

A further problem is that once the catheter has been appropriately inserted into the abdominal cavity and needle removed in many instances, unintentionally, the catheter can be dislodged or removed from its appropriate insertion point within the patient.

While it is possible to try and partially ameliorate the inadvertent withdrawal of the catheter from its insertion point by way of taping down the catheter, this presents its own problems.

Although the tubing of the catheter remains fairly resilient as the needle remains within the apparatus, once the needle is withdrawn, tubing of the catheter may become prone to folding, creasing and/or kinking or the like.

Once the tubing of the catheter becomes folded, creased, kinked or the like, the ability of the fluid to drain from the body cavity can be substantially restricted, particularly if drainage is by gravity feed.

Therefore, there is the requirement to be able to provide an arrangement which will be adapted to assist medical practitioners removing the needle from the catheter assembly, provide a better means for maintaining the catheter within its appropriate inserted position so it cannot be unintentionally dislodged and to also provide this fastened mounting position of the catheter so as to provide for the most efficient form of drainage flow within the tubing of the catheter.

Further objects and advantages of the invention will become apparent from a complete reading of the following specification.

SUMMARY OF THE INVENTION

In one form of the invention there is provided a catheter mounting arrangement for mounting a catheter to a patient, said catheter mounting arrangement including;

a main housing unit configurable to be fastenable around a catheter that has been inserted into a fluid cavity within a patient;

said main housing unit including a slot, wherein said slot defines a longitudinal opening within the main housing unit through which an uninserted section of tubing of the inserted catheter is passable there through said slot;

said main housing unit and inserted catheter including an engagement arrangement, wherein the engagement arrangement is configured so that once the uninserted section of the tubing of the inserted catheter has passed through the slot of the main housing unit the engagement arrangement provides for a fixed vertical support of the catheter within the main housing unit so that the uninserted section of tubing of the inserted catheter remains substantially upright and/or substantially free of kinks or bends within the uninserted section of tubing of the inserted catheter.

In preference the engagement arrangement between the main housing unit and the catheter to provide for the fixed vertical support of the catheter within the main housing unit so that the uninserted section of tubing of the inserted catheter remains substantially upright and/or substantially free of kinks or bends within the uninserted section of tubing of the inserted catheter, includes a longitudinal intermediate piece.

In preference the longitudinal intermediate piece includes a clip or clamp arrangement to clip or clamp onto a top section of the catheter.

In preference the main housing unit includes a hollow channel or receptacle in which the longitudinal intermediate piece is adapted to be nested therein.

In preference the intermediate piece is a longitudinal rod or column including a vertical slot along its longitudinal length, which when nested within the hollow channel or receptacle of the main housing unit, is rotatable or positioned so said vertical slot is alignable with the slot that defines the longitudinal opening within the main housing unit through which the uninserted section of tubing of the inserted catheter is passable there through.

In preference the longitudinal intermediate piece includes an external threaded configuration.

In preference the longitudinal intermediate piece external threaded configuration matches a corresponding threaded arrangement of the defined channel or receptacle within the main housing unit such that the inserted catheter can be vertically elevated and lowered up and down within the main housing unit.

In preference in an alternative embodiment of the invention the main housing unit includes a user rotatable height adjustment nut arrangement adapted to adjust the vertical height of the longitudinal intermediate piece when the longitudinal intermediate piece is mounted to the main housing unit.

In preference the user rotatable height adjustment nut arrangement is supported in a top section of the main housing unit.

In preference the user rotatable height adjustment nut arrangement includes a rib or knob extension, wherein the rib or knob extension, engages with grooves or slots of the external threaded configuration of the longitudinal intermediate piece.

In preference the user rotatable height adjustment nut arrangement is of a generally cylindrical or circular shape and includes a vertical slot, so that when the user rotatable height adjustment nut arrangement is supported within the top section of the main housing unit, it is rotatable or positioned so said vertical slot is alignable with the slot that defines the longitudinal opening within the main housing unit through which the uninserted section of tubing of the inserted catheter is passable there through.

In preference the main housing unit includes an inverted cone shape, wherein an apex of the inverted cone shape provides an opening through which the longitudinal intermediate piece is adapted to pass there through into the defined channel or receptacle within the main housing unit.

In preference the inverted cone shape of the main housing unit includes an indented shoulder around part of a periphery of the inverted cone shape.

In an alternative embodiment of the invention the main housing unit includes a more generally cylindrical shape section, wherein the more generally cylindrical shape section of the main housing unit includes the top section wherein the user rotatable height adjustment nut arrangement is supported.

In preference the main housing unit including the more generally cylindrical shape section, wherein the more generally cylindrical shape section of the main housing unit includes the top section wherein the user rotatable height adjustment nut arrangement is supported, further includes a generally flat or slightly inclined section laterally extending out there from the base of the more generally cylindrical shape section of the main housing unit.

In preference the longitudinal intermediate piece includes a resilient clip arrangement that is adapted to allow a section of the longitudinal intermediate piece to clamp on or about the catheter so as to fix the catheter to the intermediate piece.

In preference the main housing unit includes a peripheral skirt laterally extending out therefrom a base edge of the main housing unit.

In preference peripheral skirt laterally extending out therefrom the base edge of the main housing unit includes an adhesive strip.

In preference the main housing unit includes measurement units on an external face of the main housing unit.

In preference the main housing unit is transparent.

In preference the longitudinal intermediate piece is transparent.

Advantageously the catheter mounting arrangement of this invention has been able to provide a convenient means with which a medical practitioner, having inserted catheter into the patient, can then safely mount the catheter mounting arrangement in place about the catheter by way of the novel and inventive slot which defines the longitudinal opening by which the external section of the catheter can pass there through to be retained and appropriately vertically supported within the main housing unit.

The medical practitioner is able to use just a single hand to draw the catheter mounting arrangement about the inserted catheter.

In order now to describe the invention in greater detail a series of preferred embodiments will be described with the assistance of the following illustrations and accompanying text.

BRIEF DESCRIPTION OF THE DRAWINGS

FIG. 4b is a top view of the catheter mounting arrangement shown in FIG. 4a.

FIG. 4c is a front view of the catheter mounting arrangement shown in FIG. 4a.

FIG. 6b is a top view of the catheter mounting arrangement shown in FIG. 6a.

FIG. 6c is a front view of the catheter mounting arrangement shown in FIG. 6a.

DETAILED DESCRIPTION OF THE DRAWINGS

The catheter mounting arrangement for mounting an inserted catheter to a patient is shown generally as (10).

The catheter mounting arrangement (10) includes a main housing unit (12), which in the preferred embodiment is of an inverted cone configuration or shape.

Figure 2:
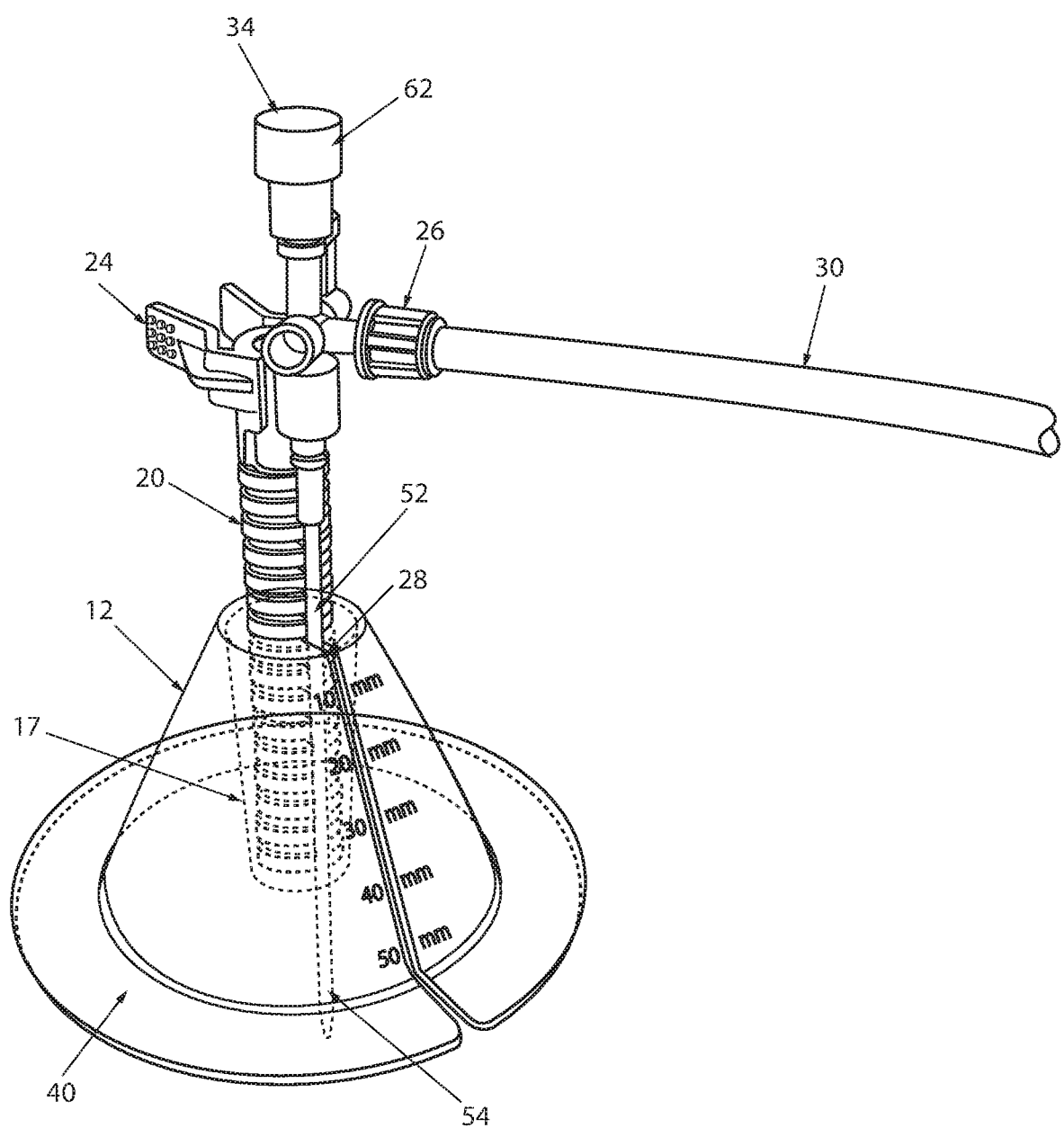
FIG. 2 is a perspective view of the catheter mounting arrangement having the inserted catheter mounted therein.

The main housing unit (12) includes an opening (16) which provides access to an internal channel (17) as best seen in FIG. 2, wherein the internal channel (17) includes threading (18), which matches with the threads (22) of the longitudinal intermediate piece (20).

The main housing unit (12) includes a slot (14) which defines the longitudinal opening (19) which will allow the external section (52) of the tubing (28) of the catheter (26) to pass there through.

Figure 1:
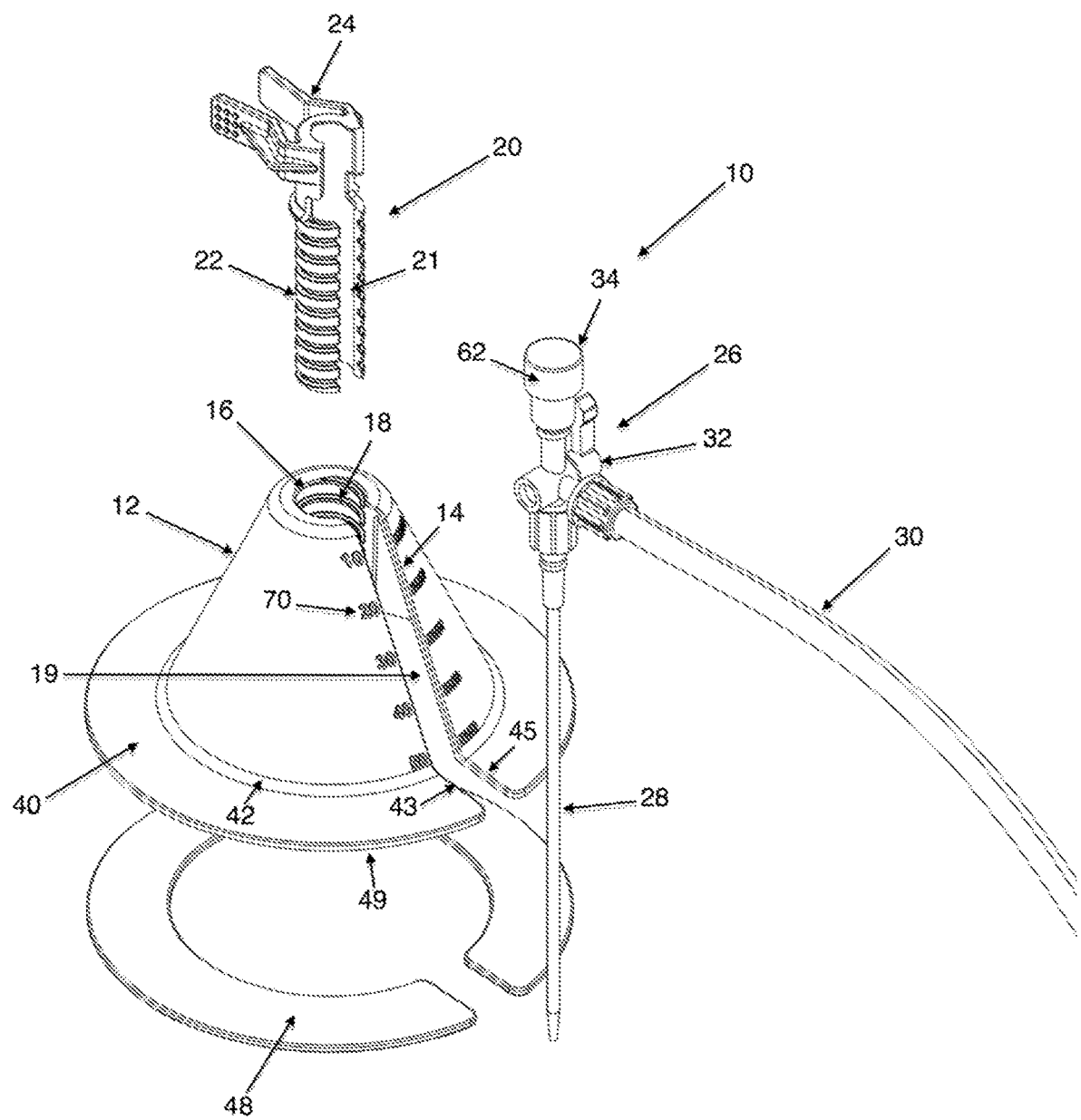
FIG. 1 is an exploded perspective view of the catheter mounting arrangement, including the catheter, to be inserted into the patient in a preferred embodiment of the invention.
Figure 3:
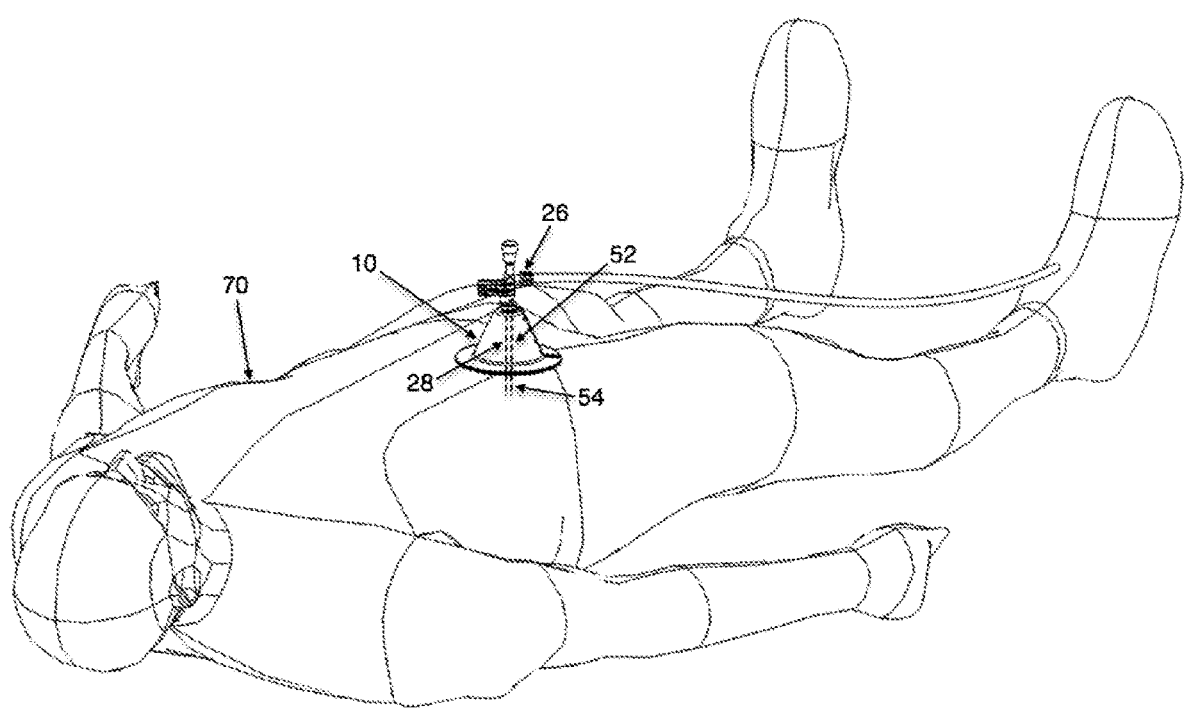
FIG. 3 is a schematic representation of the catheter mounting arrangement with a catheter inserted into a patient in a preferred embodiment of the invention.

Although not shown in FIGS. 1 and 2, so as to provide greater clarity and understanding as to how the invention works, the catheter (26) is not shown inserted into the patient as illustrated in FIG. 3. FIG. 2 assists in best explaining how the catheter (26) can be positioned within the intermediate piece (20) once the intermediate piece (20) has been threaded into the channel (17) of the main housing unit (12).

The slot (21) of the longitudinal intermediate piece (20) aligns with the corresponding slot (14) of the main housing unit (12) so that the tubing (28), or at least the external section (52) of that tubing (28) of the catheter (26) that has been inserted into the patient can then pass through the corresponding slots (14) and (21) to be fixedly engaged and held by or within the main housing unit (12).

In the preferred embodiment shown in FIGS. 1 and 2 there is a simple resilient clip mechanism (24) which is able to clasp onto the catheter (26) and hold the catheter (26) in place with the longitudinal intermediate piece (20).

The longitudinal intermediate piece (20) is already fixed and held with the main housing unit (12) by virtue of the channel (17) and the corresponding threaded arrangement (18) of the channel (17) with that of the threads (22) of the longitudinal intermediate piece (20).

The main housing unit (12) also includes a peripheral lateral extending skirt (40) which extends around the base edge (42) of the inverted cone shaped main housing unit (12) interrupted only by opposing edges (43) and (45) which maintain the opening (19) defined by the slot (14) of the main housing unit (12).

In this preferred embodiment the lateral skirt (40) about the base edge (42) of the inverted cone shaped main housing unit (12) includes an adhesive arrangement (48) connected to the underside (49) of the lateral skirt (40).

Uniquely, the inverted cone shaped main housing unit (12) allows the arrangement to be brought in about the inserted catheter (26) fastened to the patient easily and conveniently.

Having the skirt (40) not only allows improved balancing of the main housing unit (12) to the patient's body, but it also provides a location to which an adhesive strip can be attached thereto which then allows for the main housing unit (12) to be fixed to the body of the patient.

Hence rather than having unsightly, unhygienic and difficult to apply adhesive tape to stick down the catheter that has been inserted into the body of the patient, the catheter mounting arrangement of this invention inherently incorporates into its structure a means by which the adhesive can be placed on the underside of the skirting to which that skirting can also assist in balancing and maintaining the orientation of the main housing unit during movement of the patient thereby preventing unintentionally withdrawal of the inserted catheter.

Referring specifically now to FIG. 2 which further assists in understanding this invention where it is noted that the tubing (28) of the catheter (26) is represented in this illustration as having an external section of the inserted catheter tubing (28) shown as (52) which remains outside the patient and an inserted section shown as (54) of the tubing (28) represented as being within the body as shown in FIG. 2 represented with dashed lines.

In application, the catheter (26) by the appropriately qualified medical practitioner would insert the needle (not shown) and the tubing (28) of the catheter (26) into the abdominal cavity of the patient. (The patient and the abdominal cavity are not shown in FIG. 2).

However as introduced above, the section of the catheter tubing (28) represented by the dashed lines (54) is representative of that part of the tubing (28) which has been inserted into the body and ultimately into the abdominal cavity which requires drainage of fluid.

Once the catheter (26) has been inserted in that cavity within the patient then the inserted catheter can then be engaged with the catheter mounting arrangement of this invention.

The medical practitioner is able with the catheter mounting arrangement of this invention, with one hand, to bring across the main housing unit (12) with the longitudinal intermediate piece (20) mounted therein to encapsulate the tubing (28) of the catheter (26) and notably the external section represented as (52) of the tubing (28).

The external section (52) of the tubing (28) of the catheter (26) is able to be held vertically upright and prevented from folding, creasing, kinking and the like, once the needle (not shown) is withdrawn from the opening (34) which in the illustrations has the opening (34), capped with a cap (62), representative that the needle (not shown) has already been withdrawn from the catheter (26) so the opening (34) has been appropriately sealed off through cap (62). The tubing (28) and notably the external section (52) of that tubing (28) remains vertically orientated thereby maximising fluid flow.

Again, as introduced above, the actual mounting of the main housing unit (12) to the patient is done safely and conveniently, leaving an hygienic finishing through the application of the adhesive strip (48) on the underside (49) of the lateral skirt (40) of the main housing unit (12) so as to fasten the mounting of the main housing unit (12) to the patient.

The main housing unit (12) includes a series of measurement units shown generally as (70) which assists in allowing the elevation or lowering of the inserted catheter incrementally as required by way of the up and down movement afforded between the longitudinal intermediate piece (20) and the threaded hollow channel (17) defined within the main housing unit (12).

Importantly also, as the catheter (26) is able to be mounted and fixed within the main housing unit (12) allows the withdrawal of the needle (not shown) from the tubing (28) of the catheter (26) once insertion of the catheter is complete and the drainage of the fluid from the body cavity is to be commenced.

Accordingly, as introduced above, this invention provides a means by which a needle included as part of a catheter assembly inserted into a body cavity, can be removed conveniently and safely, leaving behind appropriately the tubing of the catheter in place for the requisite drainage of the fluid from the cavity.

By mounting the catheter (26) in place within the main housing unit (12) as the needle (not shown) is removed from the catheter (26) also avoids the needle puncturing organs and/or blood vessels within the patient.

Advantageously, once the inserted catheter (26) is mounted and fastened, it also prevents the patient from unintentionally having the catheter (26) dislodged or withdrawn from the body by virtue of the fastening arrangement afforded in the preferred embodiment through the adhesive strip (48) attached to the lateral skirt (40) incorporated as part of the main housing unit (12).

As the tubing (28) of the catheter (26) is able to be held upright within the cone shaped configuration of the main housing unit (12), this means that the external section (52) of the tubing (28) of the catheter (26) does not hinder or impede fluid flow.

FIG. 3 is a schematic representation illustratively showing the patient (70) to which the catheter mounting arrangement (10) of this invention has been mounted thereto once the catheter assembly (26) has been inserted into the patient (70) such that the inserted section (54) of the tubing (28) of the catheter (26) engages the abdominal cavity and to which the mounting of the catheter (26) to the catheter mounting arrangement (10) of this invention, allows the external section (52) of the tubing (28) of the catheter (26) to remain aligned and orientated without any significant folds, kinks or otherwise that would affect drainage flow there through the tubing (28) of the catheter (26).

With this invention the catheter can no longer move back into the abdomen after being manipulated which avoids an additional source of potential infection.

Traditionally all adhesive methods need to be removed in order to change or manipulate the catheter if drainage rates alter, but advantageously this invention allows the operator the flexibility to change the height of the catheter without removing the assembly from the anchorage point.

In a further preferred embodiment of the invention for the catheter mounting arrangement for mounting a catheter that has been inserted into a fluid cavity within a patient is shown in FIGS. 4a, 4b, 4c and 5a and 5b generally as (80).

For the most part the catheter mounting arrangement (80) provides the same functionality and utility as the catheter mounting arrangement referenced as (10) in FIGS. 1 to 3, differing only with slight modifications to the main housing unit and also including a feature that will be discussed in greater detail shortly below, that will allow height adjustability of the longitudinal intermediate piece.

Figure 4A:
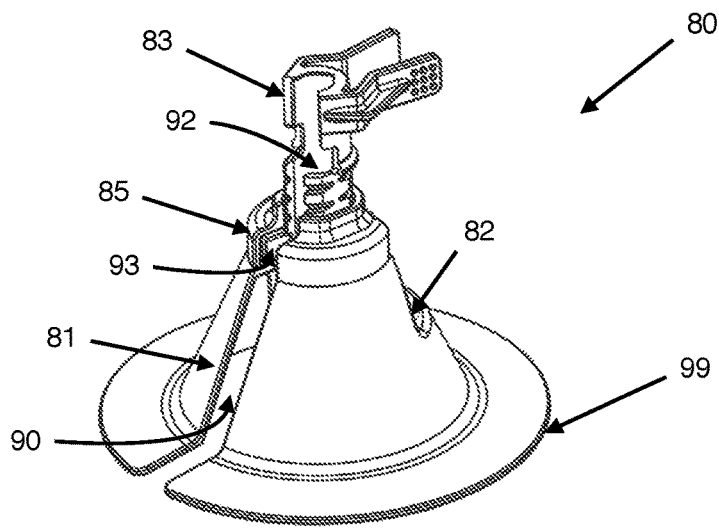
FIG. 4a is a generally upper front right-hand side perspective view of a catheter mounting arrangement in a further preferred embodiment of the invention.
Figure 4B:
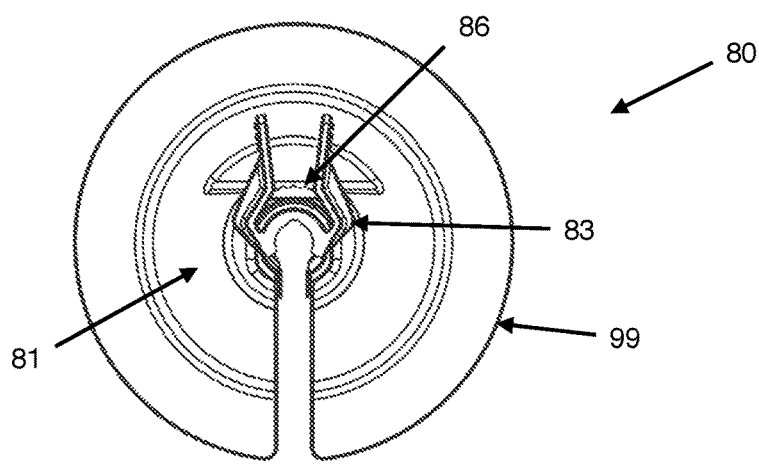
Figure 4C:
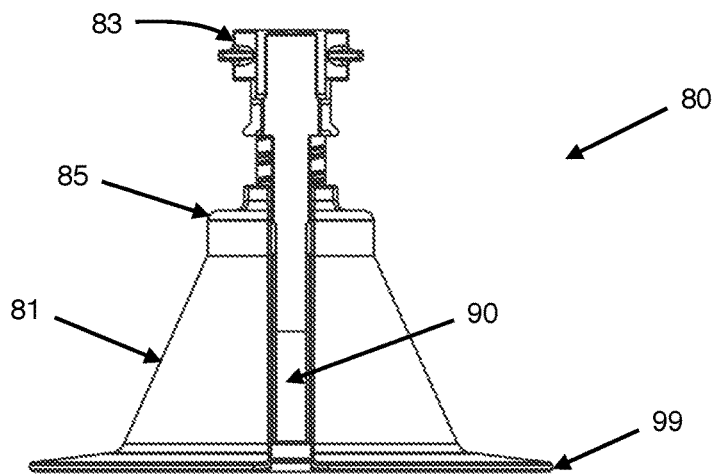
Figure 5A:
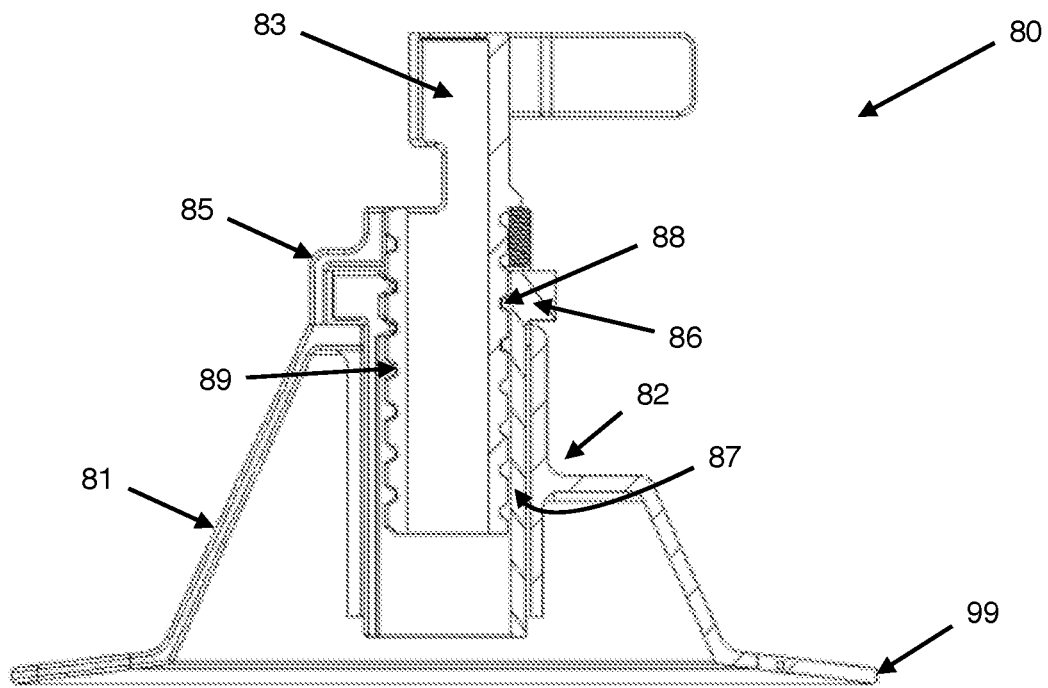
FIGS. 5a and 5b are cross-sectional views of the catheter mounting arrangement shown in FIG. 4a through to FIG. 4c with FIG. 5a showing the longitudinal intermediate piece in a retracted position and FIG. 5b showing the longitudinal intermediate piece in an extended position.
Figure 5B:
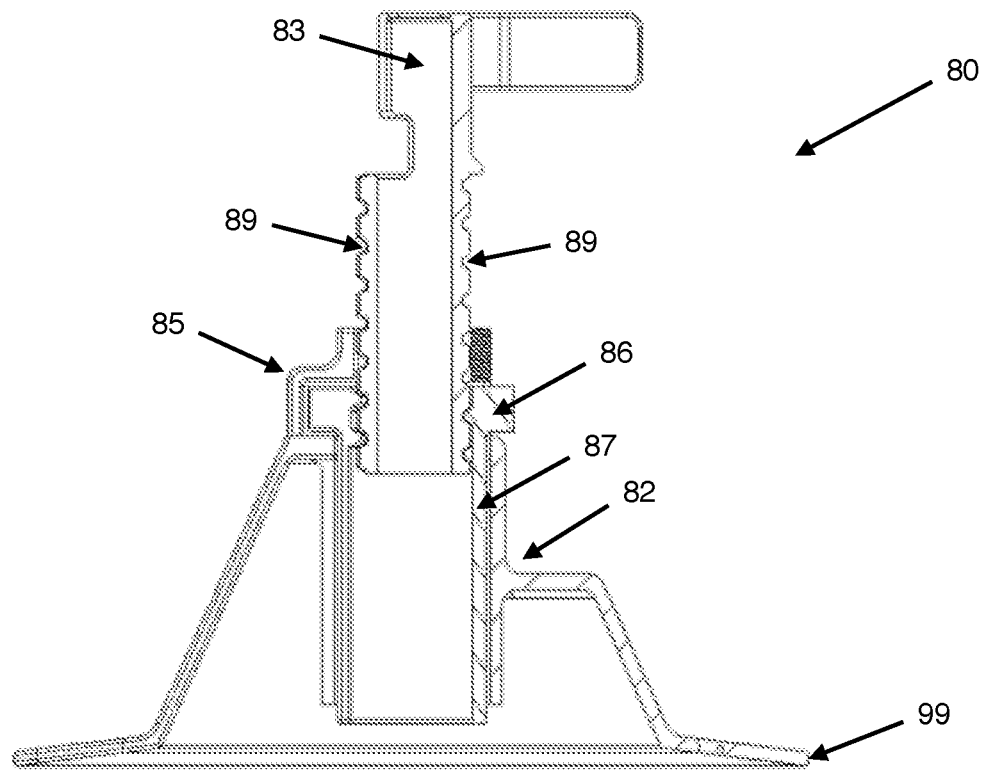

In the further preferred embodiment shown in FIG. 4a through FIG. 5b the catheter mounting arrangement (80) includes the main housing unit (81) having a generally inverted cone configuration but as best seen in FIGS. 4a, 5a and 5b, the inverted cone configuration has been slightly reconfigured to include an indented shouldered section (82) which provides further rigid support to the housing unit (81) of the catheter mounting arrangement (80).

The catheter mounting arrangement (80) also the longitudinal intermediate piece (83) which is insertable into the generally circular slot at the top of the housing unit (81).

The housing unit (81) includes a top section, that is shown generally as (85) that encloses in part a height adjustable nut (86) which is user-accessible.

The height adjustable nut (86) includes a sleeve section (87) as best seen in FIGS. 5a and 5b to which the longitudinal intermediate piece (83) can be threaded there into so as to slide and be positioned within the sleeve (87) that forms part of the user-accessible height adjustable nut (86).

In the preferred embodiment shown, the user height adjustable nut (86) includes a rib or knob extension (88) which is able to engage with the threaded external outer surface (89) of the longitudinal intermediate piece (83).

As seen in FIG. 5a, the longitudinal intermediate piece (83) is in the retracted position within the housing unit (81) of the catheter mounting arrangement (80).

Upon rotation of the height adjustable nut (86) this then allows the knob or rib (88) to engage with the grooves of the threads (89) profiled onto the external surface of the longitudinal intermediate piece (83).

As required, this allows the longitudinal intermediate piece (83) to be vertically extended up and down within that main housing unit (81) of the catheter mounting arrangement (80) even when a catheter (not shown) is clamped to the longitudinal intermediate piece (83).

Therefore for the most part the preferred embodiment shown in FIGS. 4a, 4b, 4c and 5a and 5b operate and function in the same way as the catheter mounting arrangement (10) shown in FIGS. 1 to 3 but further include the functionality of being able to adjust the height of the longitudinal intermediate piece (83) through the introduction of the height adjustable nut (86) which is incorporated into the top housing section (85) of the main housing unit (81).

Importantly, the catheter mounting arrangement (80) includes the essential main slot (90) which will allow the catheter that has already been inserted into the fluid cavity within the patient to be passable there through, the longitudinal intermediate piece (83) will also include the slot (92) which will be able to align with the corresponding slot (90) of the main housing unit (81) when the catheter has to be passed there into the housing unit (81) to be mounted upon the longitudinal intermediate piece (83).

The height adjustable nut (86) which is supported in the top housing section (85) also includes a gap within its circular body arrangement so as to provide an opening as best seen in FIG. 4a as (93) again to allow unobstructed clearance for the catheter to be able to pass through the housing unit (81) to be clamped in position upon the longitudinal intermediate piece (83), which advantageously in the preferred embodiment shown in FIGS. 4a through to 5b will allow, if necessary, height adjustability of that longitudinal intermediate piece (83) once the catheter is mounted by a user if need be through the height adjustable nut (86).

The housing unit (81) of the catheter mounting arrangement (80) in FIGS. 4a through to 5b also includes the peripheral lateral extending skirt which provides for a flexible adhesive base wherein that flexible adhesive base (99) will allow the housing unit (81) to be fixed to the body of the patient.

As introduced above, rigidity and general support of the housing unit is assisted in part by the introduction of the shouldered indent (82) profiled into the generally inverted cone shape of the housing unit (81).

FIGS. 6a, 6b, 6c, 7a and 7b provide for an example of a further preferred embodiment of the catheter mounting arrangement of this invention shown generally as (104).

Figure 6A:
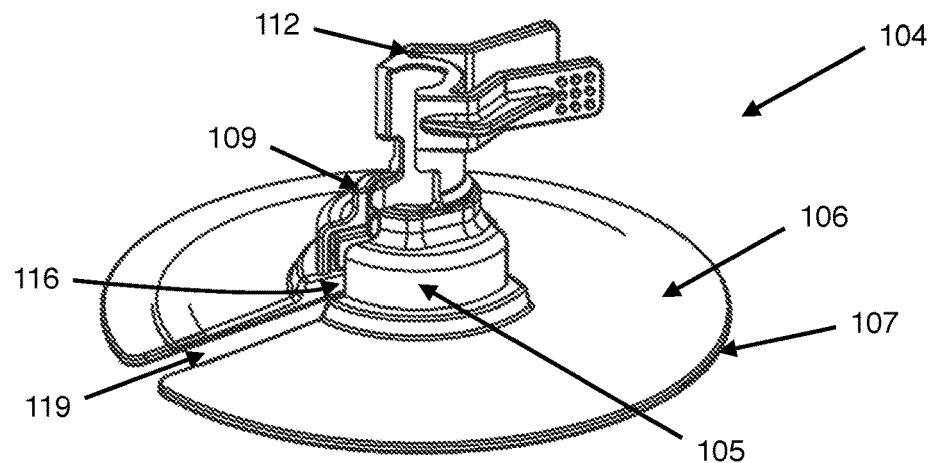
FIG. 6a is a generally upper front right-hand side perspective view of a catheter mounting arrangement in a further preferred embodiment of the invention.

The catheter mounting arrangement (104) of the preferred embodiment shown in FIGS. 6a through to 7b includes the same height adjustability of the longitudinal intermediate piece referenced and described in relation to the preferred embodiment of FIGS. 4a through to 5b with the main featured difference of the embodiment shown in FIGS. 6a through to 7b including an alternative structural arrangement to the housing unit of the catheter arrangement (104).

As seen in FIGS. 6a through to 7b, the housing unit includes a generally cylindrical shape section (105) with a generally lower profile than the inverted cone shaped housing unit (81) in FIGS. 4a through to 5b.

The cylindrical section (105) is supported by the much generally flatter rigid base section (106) which also includes the flexible adhesive base on the underside along the outer skirting (107) of this flat rigid support section (106) of the housing unit that also includes the cylindrical section (105).

The cylindrical section (105) of the housing unit also includes the same top housing section referenced in relation to the embodiment shown in FIGS. 4a through to 5b generally as (85) but in the embodiment shown in FIGS. 6a through to 7b, the top section of the housing unit is referred to as (109). The top section (109) will enclose the height adjustable nut arrangement (110) which will allow for height adjustability of the longitudinal intermediate piece (112) following the same mechanism introduced and discussed in relation to FIGS. 4a through to 5b for the catheter mounting arrangement (80).

Figure 7A:
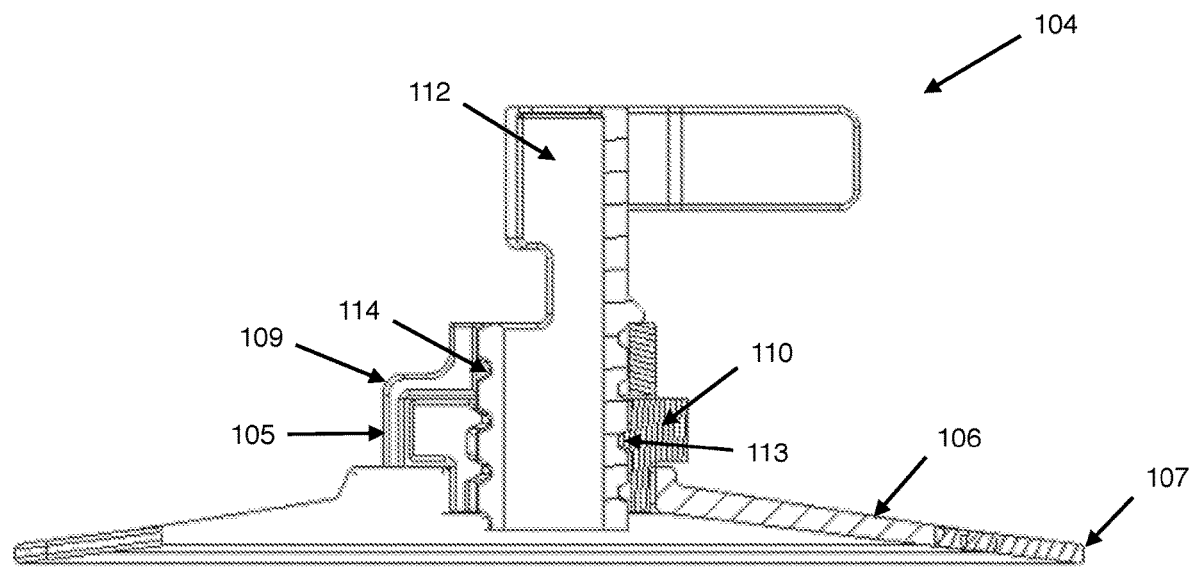
FIGS. 7a and 7b are cross-sectional views of the catheter mounting arrangement shown in FIG. 6a through to FIG. 6c with FIG. 7a showing the longitudinal intermediate piece in a retracted position and FIG. 7b showing the longitudinal intermediate piece in an extended position.
Figure 7B:
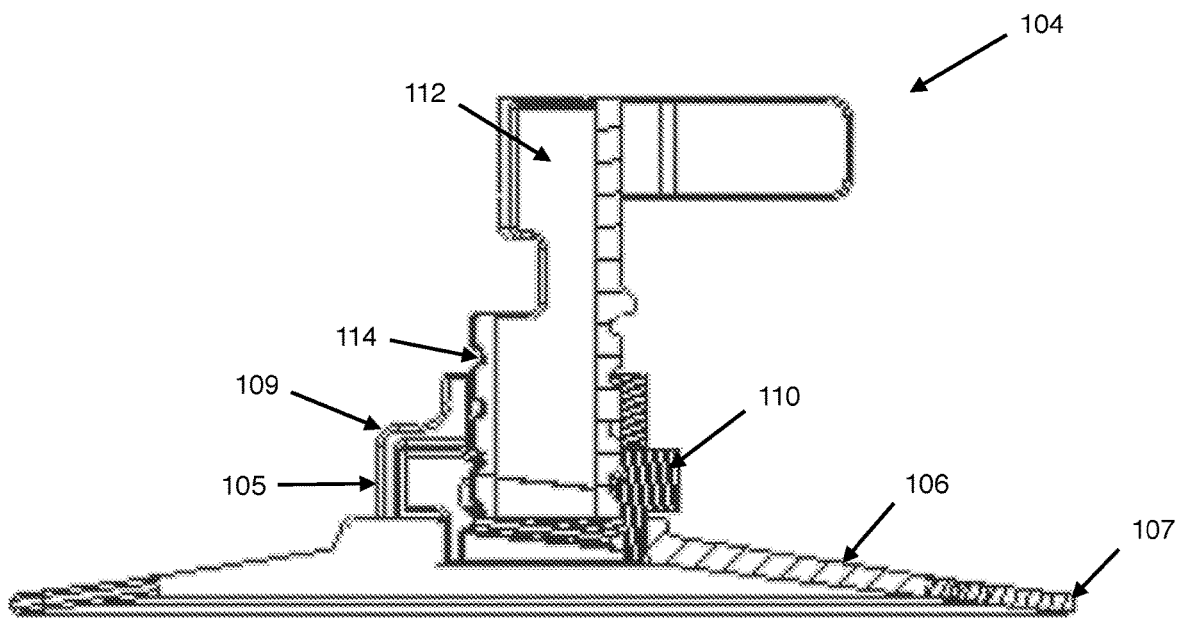

As seen in FIG. 7a the longitudinal intermediate piece (112) is in the retracted position but through rotation of the height adjustable nut (110) and notably the rib or knob extension (113) which is adapted to engage with the threaded arrangement (114) of the longitudinal intermediate piece (112) is able to place the longitudinal intermediate piece (112) in an extended position as shown in FIG. 7b.

Importantly also for the preferred embodiment shown in FIGS. 6a through to 7b, the housing unit including the cylindrical section (105) and base rigid support section (106) notably still includes the main opening slot which is shown as slot (119) in the base rigid support section (106) and (116) with the cylindrical section (105).

Figure 6B:
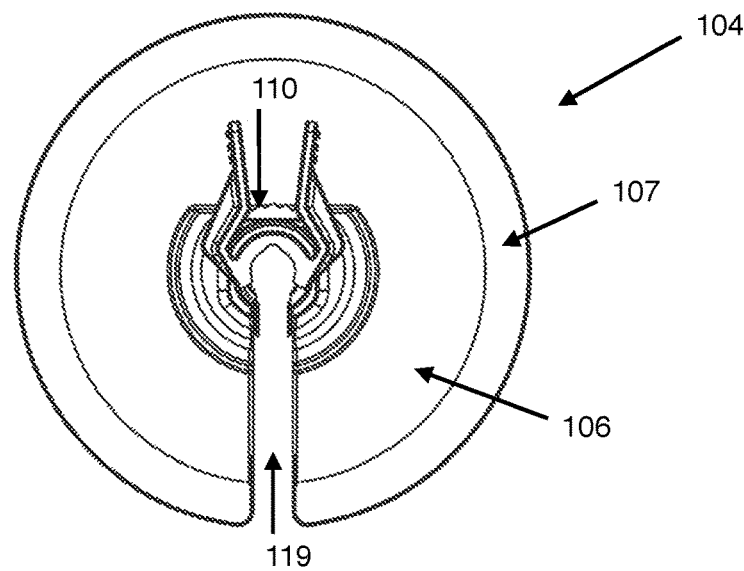
Figure 6C:
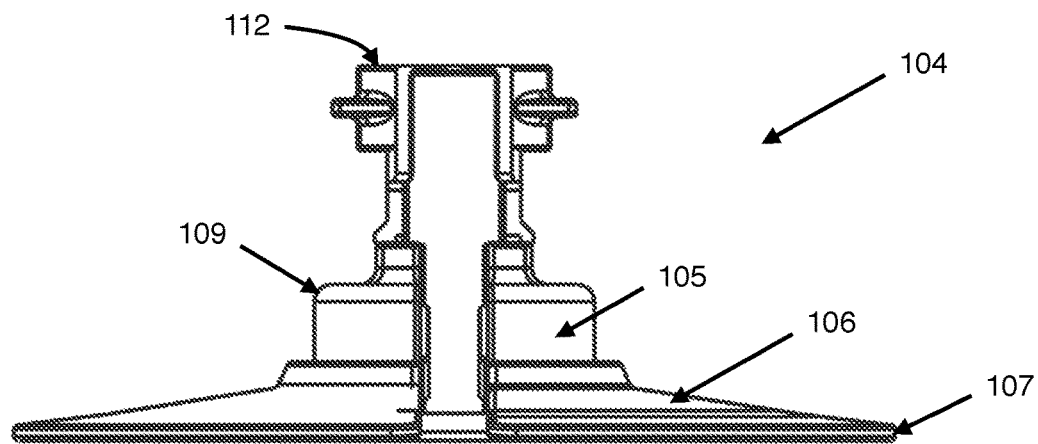

Again the longitudinal intermediate piece (112) which would clamp the catheter also includes a slot along its length and so too would the height adjustable nut (110) enclosed within the top housing section (109) including a gap or open section so that as seen in FIGS. 6a, 6b and 6c openings (119) and (116) is provided for the catheter (not shown) to pass there into the housing unit so it can be mounted and appropriately secured in place by way of the catheter mounting arrangement (104) of this invention.

The invention claimed is:

1. A catheter mounting arrangement for mounting a catheter to a patient, the catheter mounting arrangement including:
   a catheter placement housing configured to fasten around the catheter; said housing including a body having a first end and a second end, a length between said first and second ends, and a longitudinal channel along the length, said body including a longitudinal slot along an entirety of the length;
   an intermediate piece moveable within said longitudinal channel of said housing, said intermediate piece including a body having a first end and a second end, a length between said first and second ends of said intermediate piece body, and a longitudinal catheter receiving channel along the length of said intermediate piece body, said body of said intermediate piece including a longitudinal slot along the entire length, the longitudinal slots of each of said intermediate piece and said housing permitting lateral passage therethrough of at least an outer tubing associated with the catheter when said slots are rotationally aligned; and
   a collar having a thread engagement surface, said collar being configured to extend or retract the height of said intermediate piece relative to said housing.

2. The catheter mounting arrangement of claim 1, wherein said collar is configured for rotational engagement with said intermediate piece.

3. The catheter mounting arrangement of claim 1, wherein said thread engagement surface includes a rib configured to threadedly engage said intermediate piece.

4. The catheter mounting arrangement of claim 1, wherein said collar includes a threaded nut.

5. The catheter mounting arrangement of claim 1, wherein said collar has a height, and a slot along an entirety of the height, said slot of said collar being configured to permit lateral passage therethrough of at least the outer tubing of the catheter.

6. The catheter mounting arrangement of claim 1, wherein said collar includes a sleeve.

7. The catheter mounting arrangement of claim 1, wherein said intermediate piece includes a clamp at one end thereof to clamp the catheter thereto.

8. The catheter mounting arrangement of claim 1, wherein said body of said housing has a conical shape.

9. The catheter mounting arrangement of claim 1, wherein said body of said housing has a keyway through a side of said housing spaced apart from said slot of said housing.

10. The catheter mounting arrangement of claim 1, wherein said body of said housing has a flexible circumferential skirt at a base of said housing.

11. A method for adjusting a height of an intermediate piece of a catheter mounting arrangement placed on a person, comprising:
    inserting a catheter into the person;
    placing the catheter mounting arrangement about the catheter to anchor the catheter, the catheter mounting arrangement having a housing configured to house the intermediate piece and permit movement of the intermediate piece therethrough;
    clamping the catheter to the intermediate piece; and
    vertically extending or retracting the intermediate piece relative to the housing by rotating a nut relative to the intermediate piece.

12. The method of claim 11, wherein the catheter is clamped to the intermediate piece while the intermediate piece is extended or retracted.

13. The method of claim 11, further comprising withdrawing a needle associated with the catheter while the catheter is left in place in the person.

* * * * *